United States Patent
Yoon et al.

(10) Patent No.: US 8,449,725 B2
(45) Date of Patent: May 28, 2013

(54) APPARATUS FOR RECOVERING STYRENE MONOMER AND METHOD OF RECOVERING STYRENE MONOMER USING AUXILIARY SOLVENT

(75) Inventors: Byung Tae Yoon, Daejeon (KR); Myoung Jae Choi, Daejeon (KR); Seong Bo Kim, Daejeon (KR); Sang Bong Lee, Daejeon (KR)

(73) Assignee: Korea Research Institute of Chemical Technology, Daejeon (KR)

(*) Notice: Subject to any disclaimer, the term of this patent is extended or adjusted under 35 U.S.C. 154(b) by 705 days.

(21) Appl. No.: 12/694,697

(22) Filed: Jan. 27, 2010

(65) Prior Publication Data
US 2011/0067992 A1    Mar. 24, 2011

(30) Foreign Application Priority Data

Sep. 21, 2009   (KR) .................. 10-2009-0089193
Nov. 23, 2009   (KR) .................. 10-2009-0113033

(51) Int. Cl.
*C10B 1/06*    (2006.01)

(52) U.S. Cl.
USPC .............................. 202/134; 202/96; 202/118

(58) Field of Classification Search
CPC ................................... C10L 5/02; C10L 5/447
USPC .......................................... 202/96, 134, 118
See application file for complete search history.

(56) References Cited

U.S. PATENT DOCUMENTS

| | | | |
|---|---|---|---|
| 4,894,140 A * | 1/1990 | Schon | 208/72 |
| 5,608,136 A * | 3/1997 | Maezawa et al. | 588/316 |
| 6,172,275 B1 * | 1/2001 | Tadauchi et al. | 423/481 |
| 6,743,746 B1 * | 6/2004 | Prilutsky et al. | 502/185 |
| 2004/0050678 A1 * | 3/2004 | Takahashi et al. | 202/108 |
| 2007/0179326 A1 * | 8/2007 | Baker | 585/241 |
| 2009/0314622 A1 * | 12/2009 | Joo | 201/25 |

* cited by examiner

*Primary Examiner* — Nina Bhat
(74) *Attorney, Agent, or Firm* — Frommer Lawrence & Haug LLP; Ronald R Santucci; Vivek P Shankam

(57) ABSTRACT

Described are an apparatus and a method for recovering styrene monomer using an auxiliary solvent, more particularly an apparatus and a method for recovering styrene monomer through pyrolysis of waste polystyrene capable of improving recovery ratio of styrene monomer using an auxiliary solvent such as steam, preventing repolymerization of pyrolyzed styrene monomer and effectively preventing production of unwanted high molecular weight materials.

10 Claims, 5 Drawing Sheets

APPARATUS FOR RECOVERING STYRENE MONOMER AND METHOD OF RECOVERING STYRENE MONOMER USING AUXILIARY SOLVENT

CROSS-REFERENCE TO RELATED APPLICATIONS

This application claims under 35 U.S.C. §119(a) the benefit of Korean Patent Application No. 10-2009-0089193 filed Sep. 21, 2009 and No. 10-2009-0113033 filed Nov. 23, 2009, the entire contents of which are incorporated herein by reference.

TECHNICAL FIELD

The present invention relates to an apparatus and a method for recovering styrene monomer, more particularly to an apparatus and a method for recovering styrene monomer through pyrolysis of waste polystyrene.

BACKGROUND ART

With industrial development, a huge amount of plastic products are used worldwide. Last year, Korea produced about 7 million tons of general-use plastic products and became the world's 4th largest plastic producing nation. However, waste plastics are causing many environmental problems. Currently, waste plastics are mostly landfilled in the ground.

Deposition of waste plastic causes serious environmental problems such as long biodegradation time in soil, lack of landfill site, or the like. Thus, recycling of waste plastics as resources is drawing a lot of attentions. Among many solutions having been proposed for disposal of waste plastics, recycling of them as fuel oil or available feedstocks such as market chemicals is considered as the most preferable solution in aspect of economic and environment, especially compared with simple mechanical recycling followed by physical additions or processing.

Recycling of waste plastics may comprises material recycling (recycling as product material), thermal recycling (recycling into electricity, heat or other energy), and chemical recycling (recycling in the form of chemicals material such as resin material).

Physical recycling is mainly utilized in production of recycled resin, light-weight concrete, adhesive, etc. But, the newly added value by the physical recycling is not significant and recycling may be impossible after repetition of several physical recycling processes. Further, it is disadvantageous in ultimately giving a large quantity of waste polystyrene. And, the contaminated waste polystyrene foams from the wholesale markets of agricultural and fishery products or the construction sites are inappropriate for the physical recycling because they are not clean as compared to other waste polystyrene.

Moreover, because the contaminated waste polystyrene foams are about 50 times larger in volume than other waste polystyrene, those are not suitable for physical recycling, and thus have been landfilled in the ground or incinerated. However, the incineration is not environmentally friendly since dioxin or other toxic substances may be produced during the incineration.

Therefore, chemical recycling is drawing attentions. Recovery of styrene monomer from waste polystyrene was first attempted in 1997 by Nishizaki et al. It was reported that about 50% of styrene could be recovered from waste polystyrene by pyrolysis at 733 K. Since then, a lot of studies have been made to improve the yield of styrene.

FIG. 6 schematically shows a conventional process for recovery of styrene monomer from waste polystyrene by pyrolysis.

As illustrated in the figure, an existing apparatus for recovery of styrene monomer from waste polystyrene includes an injection molder, a melter, a reactor, a heat exchanger and an oil reservoir. Waste polystyrene pulverized passing through the injection molder is melted as it passes through the melter. After pyrolysis in the reactor, the resultant gas is condensed as it passed through the heat exchanger and is collected in the oil reservoir. The existing apparatus for recovery of styrene monomer is disadvantageous in that the recovery ratio of styrene monomer decreases as the pyrolysis proceeds because of residues produced from the reaction.

This will be described in more detail. According to the existing method, pyrolysis is performed continuously using a continuous stirred-tank reactor (CSTR) illustrated in FIG. 7 in order to pyrolyze the waste polystyrene melted by the melter.

As the waste polystyrene is continuously pyrolyzed in the CSTR reactor for a long time, residues are formed accumulatively and, as a result, the production of styrene monomer is interfered and the decomposed styrene monomer may react with the residue to form unwanted byproducts such as ethylbenzene, α-methylstyrene (AMS), benzene and toluene.

Also, in the existing method, the gas produced from the pyrolysis reactor is condensed by indirect cooling using a coolant. However, the indirect cooling is not so effective and styrene monomer may be repolymerized, thereby resulting in decreased yield of styrene monomer.

DISCLOSURE

Technical Problem

The present invention has been made to solve the aforesaid problems and is directed to providing an apparatus and a method for recovering styrene monomer, capable of improving yield of styrene monomer using an auxiliary solvent such as steam.

Technical Solution

To attain the object, the apparatus for recovering styrene monomer of the present invention comprises: a tubular type pyrolysis reactor for receiving waste polystyrene and pyrolyzing the same; and a cooler for cooling gas produced in the pyrolysis reactor and condensing it into oil.

Preferably, the pyrolysis reactor may include a screw which transfers the waste polystyrene. Suitably, the screw may be located substantially over the entire area of the pyrolysis reactor.

Preferably, the pyrolysis reactor may include a plurality of gas collection ports located along a moving direction of the waste polystyrene.

Preferably, the apparatus for recovering styrene monomer may further include a heater that is configured to heat the pyrolysis reactor in such a manner that the temperature at the pyrolysis reactor gets higher along the moving direction of the waste polystyrene.

Further preferably, the apparatus for recovering styrene monomer may further include an auxiliary solvent supplier which supplies an auxiliary solvent to the pyrolysis reactor. Suitably, the auxiliary solvent may comprise steam.

Yet further preferably, the pyrolysis reactor may include a plurality of auxiliary solvent injection ports aligned along the moving direction of the waste polystyrene.

Yet further preferably, the pyrolysis reactor may further include a check valve which prevents the auxiliary solvent from flowing toward the auxiliary solvent supplier.

The cooler, in which the collected gas contacts directly with cooling water, is configured to condense the collected gas into liquid.

The cooler may include a collecting mesh provided spaced apart from the position where the cooling water and the oil drop.

The cooler may further include a cooling water outlet and an oil outlet through which cooling water and the oil are discharged outward respectively after passing through the collecting mesh, and may further include a partitioning wall provided between the cooling water outlet and the oil outlet. The oil outlet may be provided between the collecting mesh and the partitioning wall.

Advantageous Effects

The present invention is advantageous in that yield of styrene monomer is not decreased even after long time of operation because residues produced from pyrolysis are not accumulated but are discharged continuously.

Further, the yield of styrene monomer is remarkably increased by using an auxiliary solvent such as steam.

Further, the yield of styrene monomer is increased because repolymerization of the pyrolyzed styrene monomer is prevented by using, for example, steam.

In addition, separation becomes easier since production of high boiling point materials such as isopropylbenzene (IPB) and α-methylstyrene (AMS) decreases.

BRIEF DESCRIPTION OF DRAWINGS

The above and other objects, features and advantages of the present invention will become apparent from the following description of preferred embodiments given in conjunction with the accompanying drawings, in which.

BEST MODE

Hereinafter, the embodiments of the present invention will be described in detail with reference to accompanying drawings.

Figure 1:
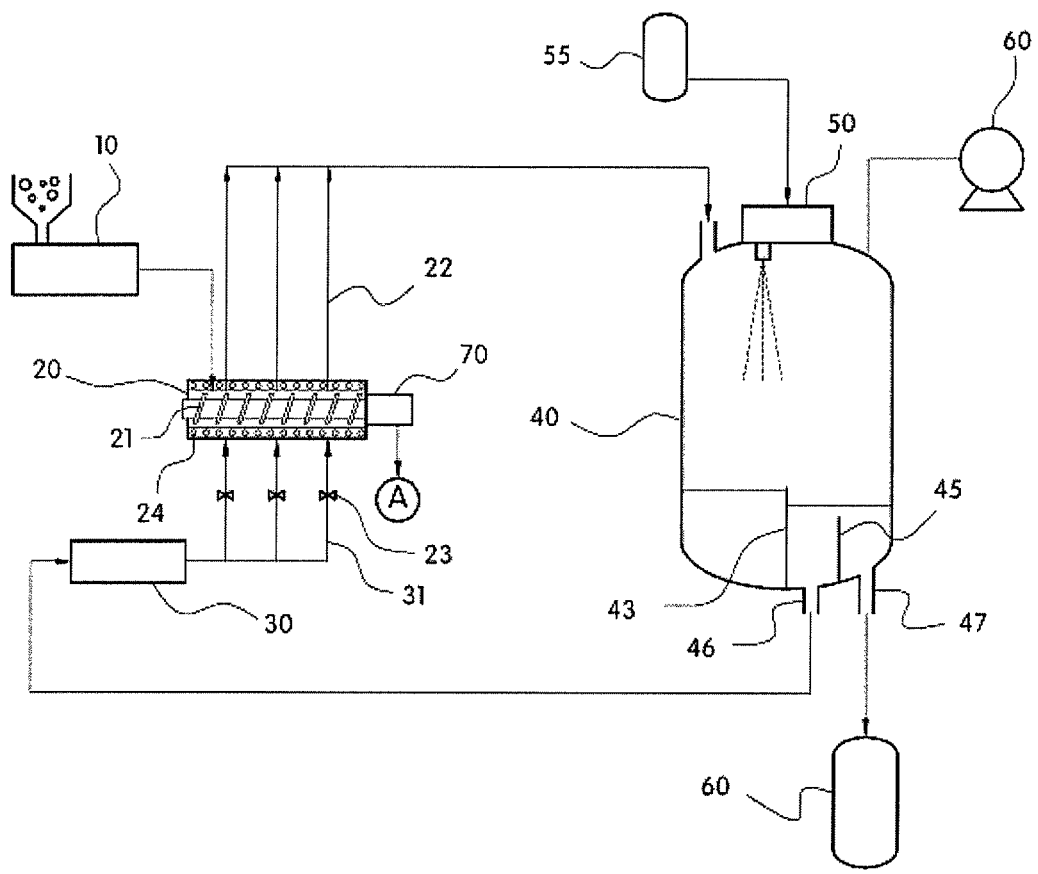
FIG. 1 schematically shows an apparatus for recovering styrene monomer according to an embodiment of the present invention.
Figure 2:
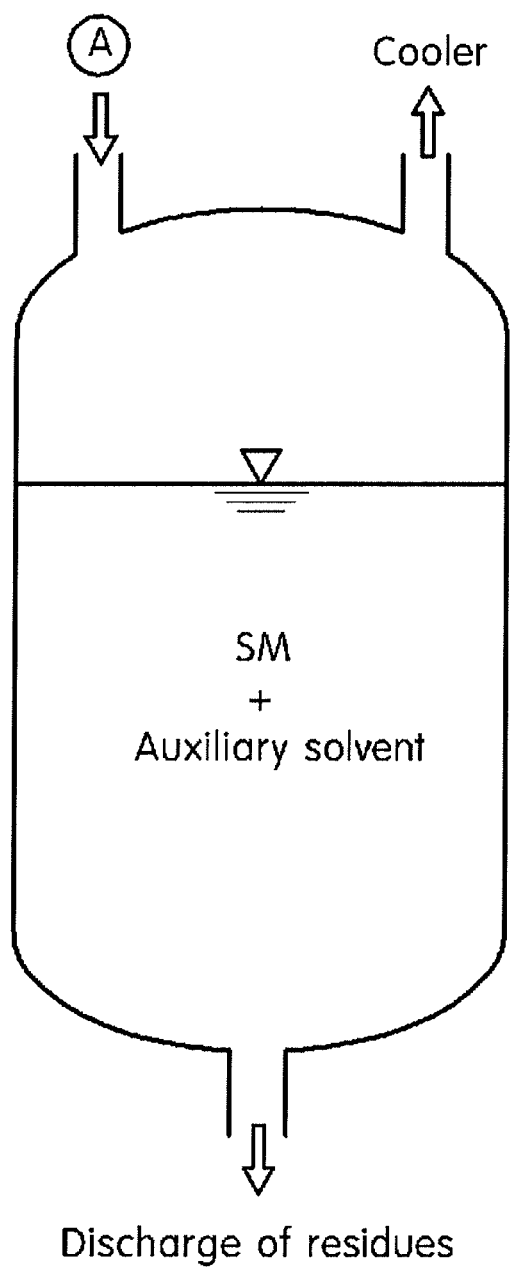
FIG. 2 is a schematic view of a secondary pyrolysis reactor, to which residue discharged from a main pyrolysis reactor is subjected, according to an embodiment of the present invention.
Figure 3:
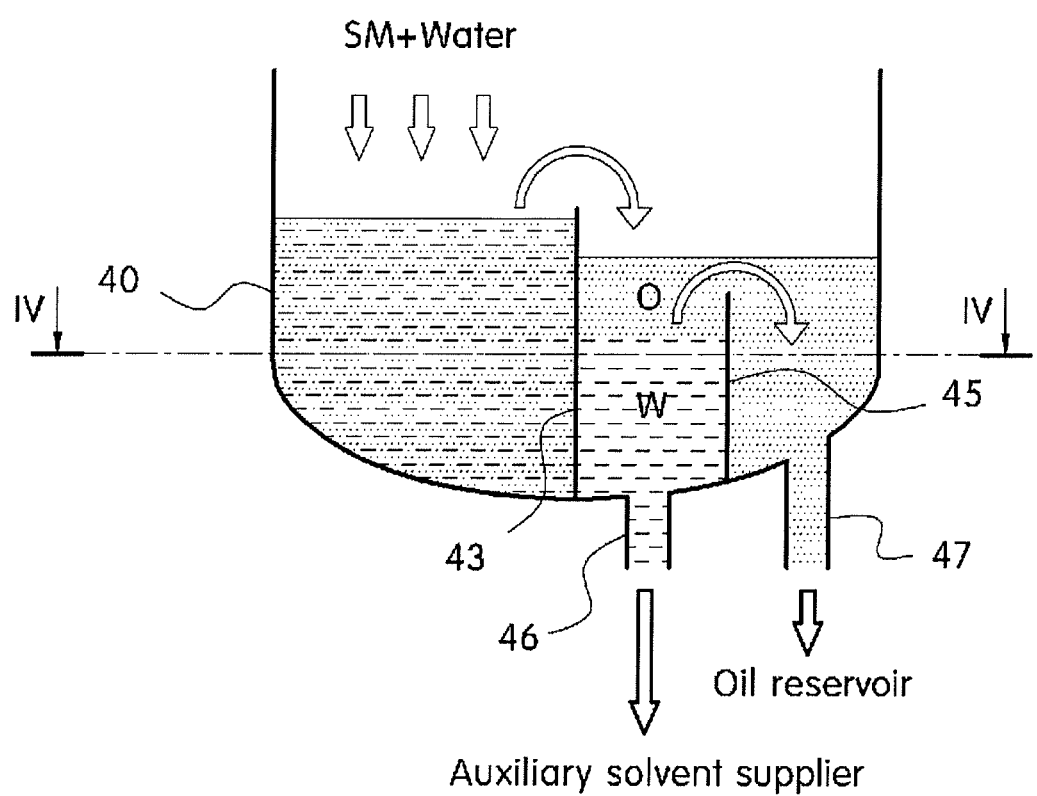
FIG. 3 schematically shows a lower portion of a cooler of an apparatus for recovering styrene monomer according to an embodiment of the present invention.

FIG. 1 schematically shows an apparatus for recovering styrene monomer according to an embodiment of the present invention, which pyrolyzes waste polystyrene and, thereby, recovers styrene monomer. FIG. 2 is a schematic view of a secondary pyrolysis reactor, to which residue discharged from a residue discharge port 70 of a main pyrolysis reactor is subjected. FIG. 3 schematically shows a lower portion of a cooler of an apparatus for recovering styrene monomer according to an embodiment of the present invention.

As illustrated in FIG. 1, an apparatus for recovering styrene monomer according to the embodiment of the present invention comprises a melter 10 which heats and melts pulverized solid waste polystyrene, a pyrolysis reactor 20 in which the molten waste polystyrene and an auxiliary solvent supplied from an auxiliary solvent supplier 30 mixed together and produces styrene monomer gas by pyrolysis, a cooler 40 for condensing the gas produced from the pyrolysis, and an oil reservoir 60 for storing the condensed styrene monomer oil. The pyrolysis reactor 20 comprises a heater 24 to control the temperature of the reactor, a screw 21 to transfer the molten waste polystyrene and the auxiliary solvent, gas collection ports 22 which collect the gas produced from the pyrolysis, a check valve 23 to prevent the molten waste polystyrene from flowing toward the auxiliary solvent supplier 30 through auxiliary solvent injection ports 31, and the auxiliary solvent injection ports 31 through which the auxiliary solvent such as steam is supplied to the pyrolysis reactor 20.

The melter 10 is fed with pulverized waste polystyrene having a predetermined size (e.g., about 2 cm) via, for example, a hopper and converts it into molten waste polystyrene. To melt the waste polystyrene, the melter 10 heats it at a predetermined temperature. If the temperature is not sufficient to melt all the waste polystyrene, some of them may remain unmelted. On the other hand, if the temperature is too high, pyrolysis may occur in the melter. Thus, it is preferred to select an appropriate temperature range. Although waste polystyrene particles are melted below 200° C., heating to this temperature may result in insufficient melting and difficulty in transfer. Also, considering that the pyrolysis of polystyrene begins at 350° C., it is preferred to heat the waste polystyrene at a temperature between 250° C. and 350° C. In another embodiment, melting and pyrolysis may be performed in the pyrolysis reactor 20, without using the melter 10.

The waste polystyrene melted in the melter 10 is introduced into the pyrolysis reactor 20 and undergoes pyrolysis. In order to increase recovery yield of styrene monomer and prevent repolymerization of the pyrolyzed styrene monomer and formation of unwanted polymer materials such as benzene, α-methylstyrene (AMS), ethylbenzene, etc., an auxiliary solvent is supplied into the pyrolysis reactor 20 by means of the auxiliary solvent supplier 30.

In the pyrolysis reactor 20, the molten waste polystyrene undergoes pyrolysis and, as a result, a mixture gas of the styrene monomer and the auxiliary solvent is produced. The gas is collected through the plurality of gas collection ports 22 provided at an upper portion of the pyrolysis reactor 20. Since the styrene monomer is collected as soon as it is produced, unwanted repolymerization may be prevented and the gas may be effectively collected until the last moment.

The pyrolysis reactor 20 is an extended tubular type reactor. Disposed inside the pyrolysis reactor 20 is a screw 21 that forcibly transfers the molten material while rotating. The screw 21 extends over the substantially entire area of the reactor. The screw 21 may preferably be a twin screw type.

The temperature of the pyrolysis reactor 20 is controlled by the heater 24 installed outside thereof. The heater 24 is configured to heat the pyrolysis reactor 20 in such a manner that the temperature at the pyrolysis reactor gets higher along the moving direction of the waste polystyrene. By making the temperature increase with the progress of reaction, reaction yield is improved and control of conversion rate becomes easy.

During pyrolysis, the auxiliary solvent serves as a barrier between the pyrolyzed styrene monomers, thereby preventing repolymerization of the pyrolyzed styrene monomers. Also, it serves as a carrier aiding discharge of the pyrolyzed styrene monomer. In addition, it prevents the pyrolyzed styrene monomer from binding with other material to form high boiling point materials such as isopropylbenzne (IPB), AMS, etc., thereby improving yield of styrene monomer.

As such, performing pyrolysis with addition of the auxiliary solvent is advantageous in that the repolymerization of the styrene monomer is prevented, the pyrolyzed styrene monomer may be recovered quickly, and the yield of styrene monomer may be remarkably improved since the production of high boiling point materials is prevented. The yield of pyrolysis may be further improved if the auxiliary solvent is supplied through a plurality of injection ports 31. In the embodiment, the plurality of injection ports 31 may be provided along the moving direction of the waste polystyrene.

Since the gas is collected through the plurality of gas collection ports 22, the residing time of the gas in the pyrolysis reactor 20 can be reduced, and conversion or polymerization into unwanted materials is effectively obviated. In a preferable embodiment, the plurality of gas collection ports 22 may be provided along the moving direction of the waste polystyrene.

During the operation of the pyrolysis reactor 20, the pressure inside the pyrolysis reactor 20 may possibly be higher than that of the auxiliary solvent supplier 30. In this case, the molten waste polystyrene in the pyrolysis reactor 20 may flow toward the auxiliary solvent supplier 30 through the auxiliary solvent injection ports 31 and may be stuck in the auxiliary solvent injection ports 31. The check valve 23 prevents the molten waste polystyrene in the pyrolysis reactor 20 from flowing toward the auxiliary solvent supplier 30. The check valve 23 may be of various conventional types, including a spring-ball type valve.

Suitably, the auxiliary solvent may be an inert material or a material not reacting with the styrene monomer. For example, it may be steam, nitrogen, toluene, or the like. Among them, steam is appropriate as the auxiliary solvent in that cooling water may be used to condense the collected gas, separation of the auxiliary solvent from the reaction product is easy and cooling process becomes simple. Instead of using steam itself, water may be introduced and vaporized by heat of the pyrolysis reactor 20 to be converted into steam.

The gas produced from the pyrolysis is directed to a cooler 40 and is cooled therein. In the embodiment, the cooling may be performed by direct cooling.

Direct cooling is a method of cooling and condensing the collected gas by spraying cooling water directly to the gas. Such a direct cooling is appropriate in case where steam is employed as the auxiliary solvent, since it is easy to separate the auxiliary solvent and cooling water from the resulting materials. In addition, the direct cooling method is advantageous in that cooling is fast, design of the cooler is simple because exposure time to high temperature is short, and recovery yield of the styrene monomer may be further improved since the cooling water and the auxiliary solvent are the same material, i.e. water.

As an example of the direct cooling, a reservoir may be provided to supply steam as the auxiliary solvent and cooling water at once. Alternatively, another reservoir may be provided to supply cooling water. In case of the embodiment illustrated in FIG. 1, a cooling water reservoir 55 may be provided to supply cooling water to a cooling water supplier 50. The cooling water supplier 50 may be provided at an upper portion of the cooler 40 and may spray the cooling water over a wide area, so that the collected gas may be effectively cooled.

Figure 4:
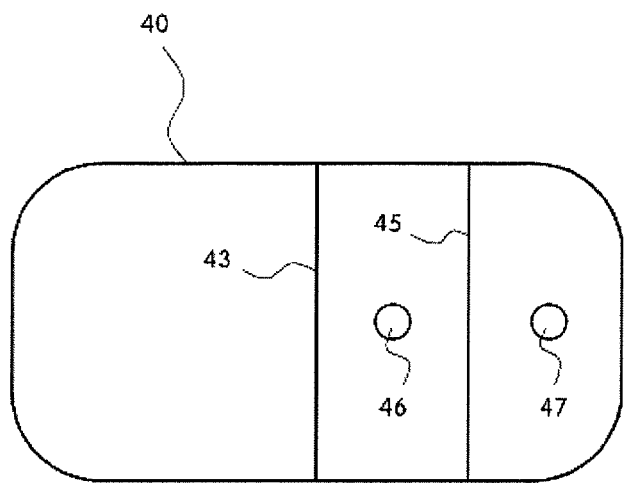
FIG. 4 is a cross-sectional view along line IV-IV of FIG. 3.

FIG. 4 is a cross-sectional view of the cooler of FIG. 3, taken along line IV-IV. The gas produced from the pyrolysis is introduced from a side of the cooler 40, cooled by sprayed cooling water, and is collected at a space defined at a left side of a collecting mesh 43. The collecting mesh 43 separates water and oil components and forwards each of them to the right side thereof. As a result, on the right side of the collecting mesh 43, water (relatively heavy) is positioned below oil (relatively light). The oil positioned at an upper portion floods over a partitioning wall 45 and then moves to the rightmost space where an oil outlet 47 is provided. In this manner, the oil may be transferred to the oil reservoir through the oil outlet 47, whereas the water is transferred to the auxiliary solvent supplier 30 through a cooling water outlet 46. Although not specifically shown in the figure, the oil is separated into the styrene monomer and other materials through steam distillation or other process.

In another embodiment, the water discharged through the cooling water outlet 46 may preferably be transferred to the cooling water reservoir 55 or may be used for other purposes.

In yet another embodiment, the cooler 40 may cool the collected gas by indirect cooling. The indirect cooling may be performed by compressing and evaporating a coolant and cooling the collected gas using the evaporation heat of the coolant. The indirect cooling method may be applicable when the auxiliary solvent is nitrogen or toluene.

At one end of the pyrolysis reactor 20, the residue discharge port 70 is furnished, through which residues resulting from the pyrolysis are continuously discharged.

As a result of the pyrolysis, high boiling point materials and pyrolysis residues are produced in addition to the styrene monomer. Since these residues interfere with the pyrolysis and reduces the yield of styrene monomer, the yield of styrene monomer tends to decrease after a long operation time.

In the embodiment of the present invention, the residue is continuously discharged through the residue discharge port 70 using the screw 21. As a result, the yield of styrene monomer does not decrease even after long operation. With the existing batch type apparatus, operation has to be interrupted for removal of the residue, which is disadvantageous in operation continuity and effectiveness. In contrast, the present invention enables continuous and effective operation because the residue is continuously discharged.

FIG. 2 is a schematic view of a secondary pyrolysis reactor, to which residue discharged from the pyrolysis reactor 20 is subjected. Since the residues discharged from the pyrolysis reactor 20 may still comprises depolymerized styrene monomer and/or not-yet-depolymerized styrene even after the pyrolysis, the secondary pyrolysis reactor 25 is provided to improve the yield of styrene monomer.

A vacuum pump 60 provided at one side of the pyrolysis reactor 20 decreases the pressure inside the cooler 40, so that the collected gas may be effectively transferred to the cooler 40 due to the pressure difference. In another embodiment, the vacuum pump 60 may not be employed.

Figure 5:
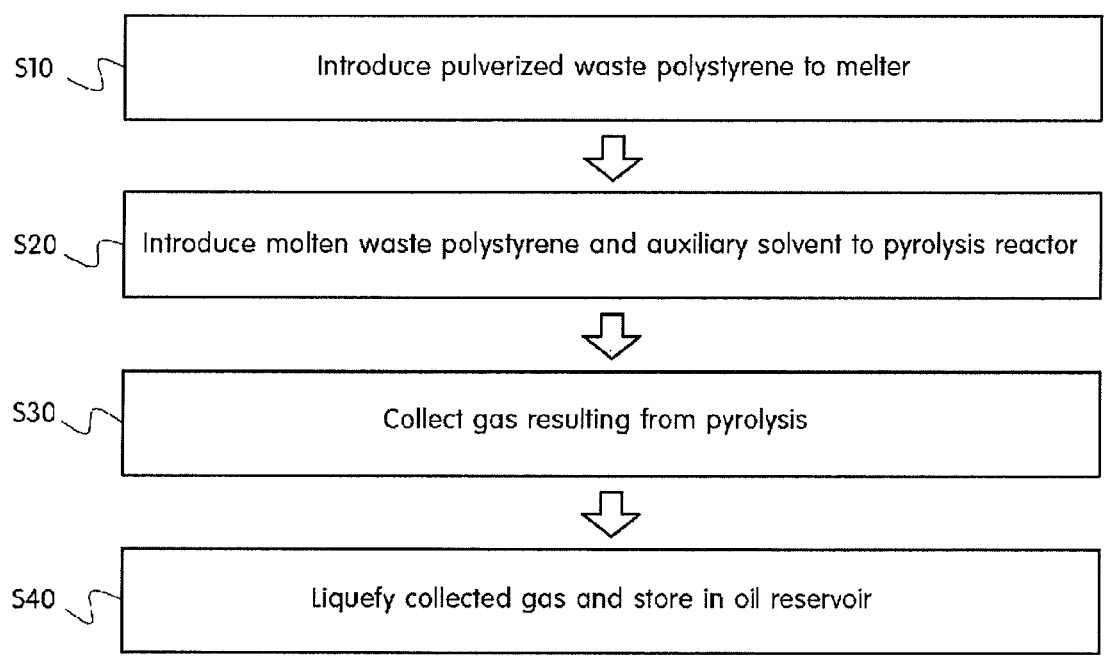
FIG. 5 is a flow diagram illustrating a method for recovering styrene monomer according to an embodiment of the present invention.
Figure 6:
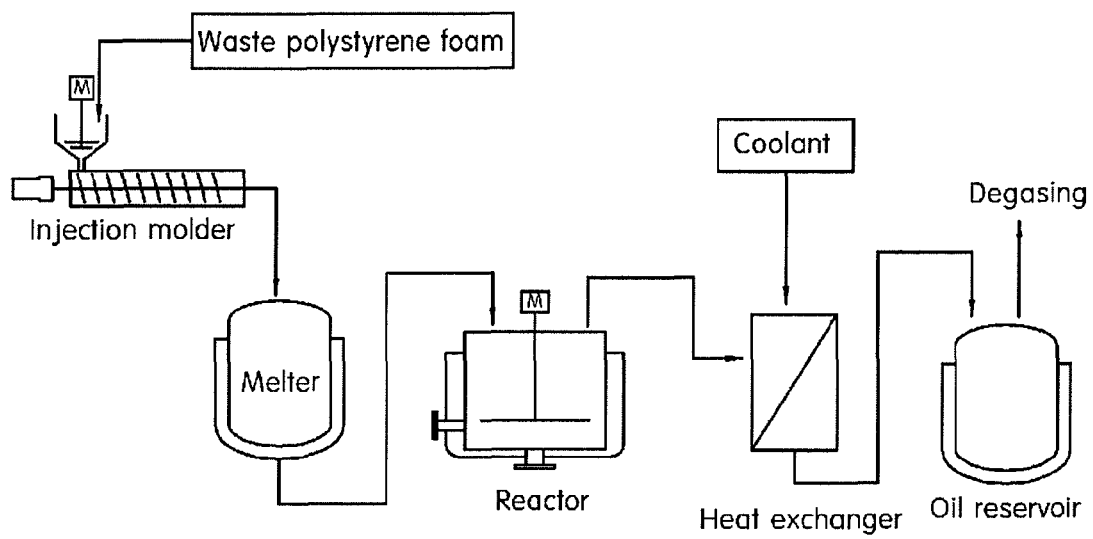
FIG. 6 schematically shows an apparatus for recovering styrene monomer according to a prior art.
Figure 7:
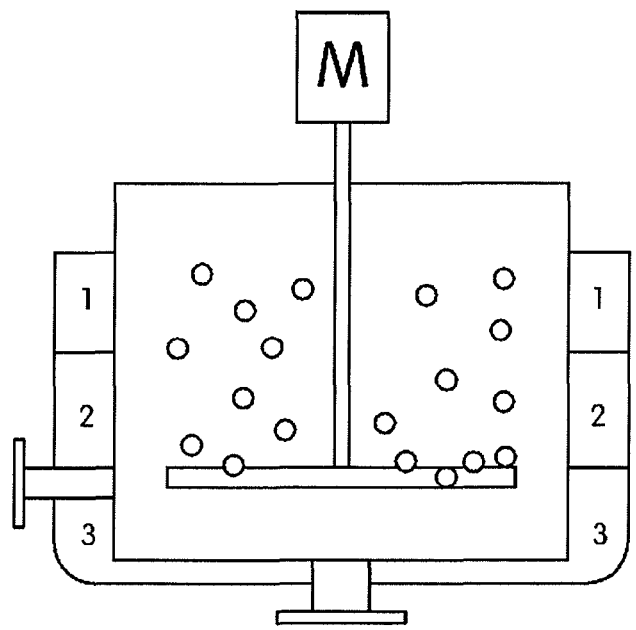
FIG. 7 shows a continuous stirred-tank reactor (CSTR) according to a prior art.

FIG. 5 is a flow diagram illustrating a method of recovering styrene monomer according to the present invention. The method comprises steps of introducing pulverized waste polystyrene to the melter 10 by means of, for example, a hopper (S10), supplying the waste polystyrene melted in the melter 10 to the pyrolysis reactor 20 together with the auxiliary solvent (S20), performing pyrolysis of the auxiliary solvent and the waste polystyrene at a predetermined temperature and collecting the resulting gas through the plurality of collection ports (S30), and condensing the collected gas and storing it in the oil reservoir (S40).

Mode for Invention

The examples and experiments will now be described. The following examples and experiments are for illustrative purposes only and not intended to limit the scope of this disclosure.

Example 1

Crushed ingot foam collected from the Garak Agricultural and Fishery Products Wholesale Market (Seoul, Korea) was used as waste polystyrene.

The collected waste polystyrene was pulverized to a size of about 1 cm and 2 kg was introduced to a hopper. Then, pyrolysis was performed while operating twin screws at a constant speed. The pyrolysis temperature was controlled to rise from 370° C. to 380° C. and to 390° C. along the moving direction of the waste polystyrene. During the pyrolysis, 0.1 part by weight of steam was injected based on the waste polystyrene.

The volume of the produced oil was measured using a graduated cylinder to monitor the extent of pyrolysis.

Example 2

The procedure of Example 1 was repeated, except that 0.5 part by weight of steam was injected based on the waste polystyrene.

Example 3

The procedure of Example 1 was repeated, except that 1.0 part by weight of steam was injected based on the waste polystyrene.

Example 4

The procedure of Example 1 was repeated, except that 1.5 parts by weight of steam was injected based on the waste polystyrene.

Tables 1 and 2 show the results of Examples 1 to 4.

TABLE 1

Composition change of oil obtained from pyrolysis of waste polystyrene

| | Oil conversion rate (%) | Residue (%) |
|---|---|---|
| Example 1 | 94 | 6 |
| Example 2 | 96 | 4 |
| Example 3 | 98 | 2 |
| Example 4 | 98 | 2 |

TABLE 2

Composition change of oil obtained from pyrolysis of waste polystyrene

| | Benzene | Toluene | Ethylbenzene | Styrene | AMS | Dimer & trimer |
|---|---|---|---|---|---|---|
| Example 1 | 0.16 | 1.61 | 4.22 | 56.90 | 7.22 | 29.89 |
| Example 2 | 0.12 | 1.51 | 4.26 | 56.39 | 7.01 | 30.71 |
| Example 3 | 0.13 | 1.53 | 4.26 | 59.94 | 6.70 | 27.44 |
| Example 4 | 0.19 | 4.00 | 5.68 | 53.96 | 7.25 | 28.92 |

As seen in Tables 1 and 2, conversion rate was very high ($\geq$94%) and styrene content was 53% or higher in all cases.

The present application contains subject matter related to Korean Patent Application No. 10-2009-113033, filed in the Korean Intellectual Property Office on Nov. 23, 2009, the entire contents of which is incorporated herein by reference.

While the present invention has been described with respect to the specific embodiments, it will be apparent to those skilled in the art that various changes and modifications may be made without departing from the spirit and scope of the invention as defined in the following claims.

The invention claimed is:

1. An apparatus for recovering styrene monomer, comprising: a supply means for supplying waste polystyrene; a tubular type pyrolysis reactor for receiving waste polystyrene from the supply means and pyrolyzing the same, the reactor comprising a residue discharge means for discharging residue resulting from the pyrolysis; an auxiliary solvent supplier for supplying an auxiliary solvent to the pyrolysis reactor, wherein the auxiliary solvent comprises steam; and a cooler, connected to the reactor via a connecting means, for cooling gas produced from the pyrolysis, and condensing the gas into styrene monomer oil.

2. The apparatus for recovering styrene monomer according to claim 1, wherein the pyrolysis reactor comprises a screw which transfers the waste polystyrene.

3. The apparatus for recovering styrene monomer according to claim 2, wherein the screw is located substantially over the entire area of the pyrolysis reactor.

4. The apparatus for recovering styrene monomer according to claim 1, wherein the pyrolysis reactor comprises a plurality of gas collection ports located along a moving direction of the waste polystyrene.

5. The apparatus for recovering styrene monomer according to claim 1, further comprising a heater that is configured to heat the pyrolysis reactor in such a manner that the temperature at the pyrolysis reactor gets higher along the moving direction of the waste polystyrene.

6. The apparatus for recovering styrene monomer according to claim 1, wherein the pyrolysis reactor comprises a plurality of auxiliary solvent injection ports aligned along the moving direction of the waste polystyrene.

7. The apparatus for recovering styrene monomer according to claim 6, wherein the pyrolysis reactor further comprises a check valve which prevents the auxiliary solvent from flowing toward the auxiliary solvent supplier.

8. The apparatus for recovering styrene monomer according to claim 1, wherein the cooler, in which the collected gas contacts directly with cooling water, is configured to condense the collected gas into liquid.

9. The apparatus for recovering styrene monomer according to claim 8, wherein the cooler comprises a collecting mesh provided spaced apart from the position where the cooling water and the oil drop.

10. The apparatus for recovering styrene monomer according to claim 9, wherein the cooler further comprises a cooling water outlet and an oil outlet through which cooling water and the oil are discharged outward respectively after passing through the collecting mesh, and further comprises a partitioning wall provided between the cooling water outlet and the oil outlet, the oil outlet being provided between the collecting mesh and the partitioning wall.

* * * * *